US00PP30850P3

(12) United States Plant Patent
Ioriatti

(10) Patent No.: US PP30,850 P3
(45) Date of Patent: Aug. 27, 2019

(54) ***RUBUS* PLANT NAMED 'BP 1522'**

(50) Latin Name: *Rubus idaeus*
Varietal Denomination: BP 1522

(71) Applicant: Berryplant di Grisenti Maria Maddalena & C. Società Semplice Agricola, Trento (IT)

(72) Inventor: Diego Ioriatti, Trento (IT)

(73) Assignee: Berryplant di Grisenti Maria Maddalena & C. Società Semplice Agricola, Trento (IT)

( * ) Notice: Subject to any disclaimer, the term of this patent is extended or adjusted under 35 U.S.C. 154(b) by 0 days.

(21) Appl. No.: 15/998,258

(22) Filed: Jul. 23, 2018

(65) Prior Publication Data

US 2019/0098814 P1 Mar. 28, 2019

(30) Foreign Application Priority Data

Sep. 25, 2017 (QZ) ..... PBR 2017/2350

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
See application file for complete search history.

*Primary Examiner* — Annette H Para
(74) *Attorney, Agent, or Firm* — The Webb Law Firm

(57) ABSTRACT

A new and distinct cultivar of *Rubus* plant named 'BP 1522' having a short growth habit and easy to pick fruits.

8 Drawing Sheets

Botanical classification: *Rubus idaeus.*
Varietal denomination: 'BP 1522'.

BACKGROUND OF THE INVENTION

The present invention comprises a new and distinct cultivar of *Rubus idaeus* (raspberry variety) known by the varietal name 'BP 1522'.

The new variety was discovered in September of 2015 in Trento, Italy as part of a planned breeding program. The purpose of the breeding program was to develop early ripening primocane raspberry varieties with excellent fruit quality and reduced crop costs when compared to currently available primocane raspberry varieties. The new variety is the result of a cross between raspberry variety 'Regina' (female parent, unpatented in the United States, CPVO Grant No. 39542) and an unnamed raspberry variety (male parent, unpatented). When compared to 'Regina', the new variety exhibits an overall shorter growth habit due to a combination of its shorter plant height and laterals. The new variety is similar to its parental varieties in exhibiting a strong primocane trait, early fruit ripening, conical fruit shape, as well as in fruit size and taste. Further, when compared to raspberry variety named 'Sugana' (U.S. Plant Pat. No. 21,357), 'BP 1522' exhibits shorter canes and laterals, dryer fruits, and improved fruit consistency (especially when harvested in warmer periods). The new variety was first asexually reproduced by root cuttings in Trento, Italy in January of 2016. Continued observations of asexual reproductions of the new variety have confirmed that the distinguishing features of this new cultivar come true, remain stable, and are retained through successive propagations.

The following traits are determined to be basic characteristics of this new cultivar which distinguish this raspberry plant as new and distinct when compared to other raspberry varieties known to the breeder:

1. Conical fruits;
2. Excellent flavor;
3. Easy to pick—even when still pink in color;
4. Big drupelets that are slightly opaque;
5. Medium-sized, dark-colored, downward sloping thorns; and
6. Short canes and laterals—canes are almost 20 cm shorter than most modern primocane raspberry varieties.

DESCRIPTION OF THE DRAWINGS

The accompanying photographic drawings illustrate the new cultivar taken at approximately one year of age, with the colors being as nearly true as possible with color illustrations of this type.

DESCRIPTION OF THE NEW PLANT

Figure 1:
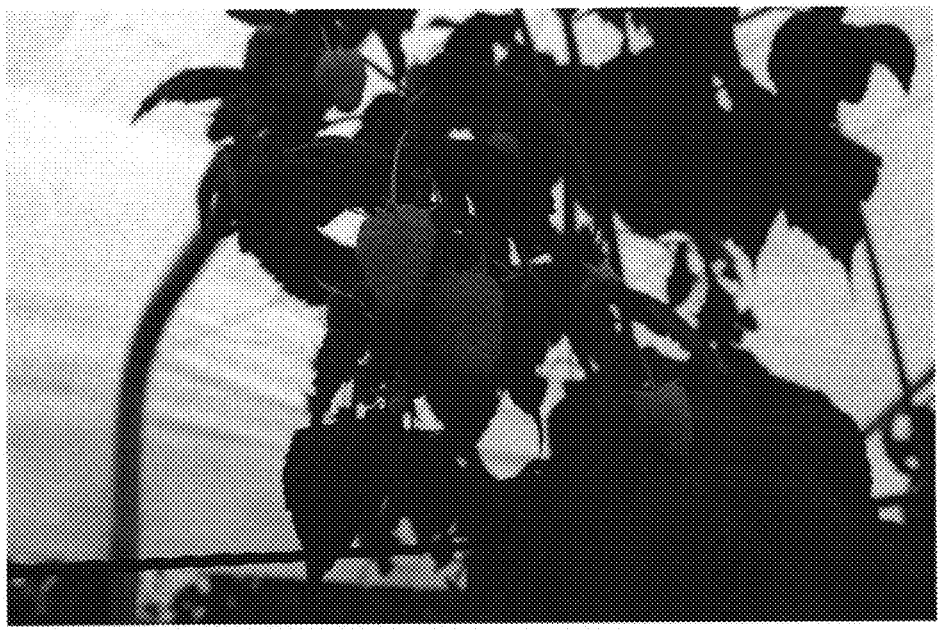
FIG. 1 illustrates the fruits of the new variety.
Figure 2:
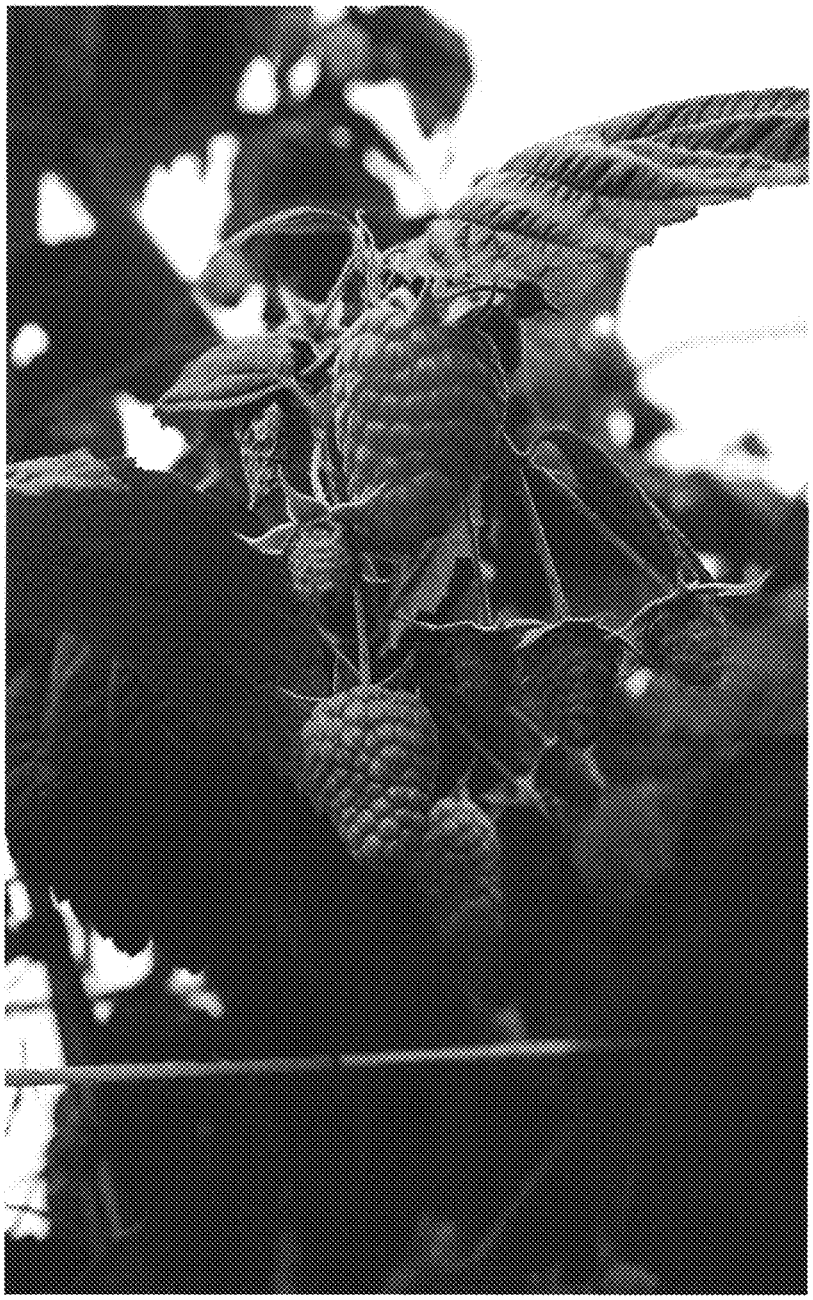
FIG. 2 illustrates the mature and immature fruits of the new variety.
Figure 3:
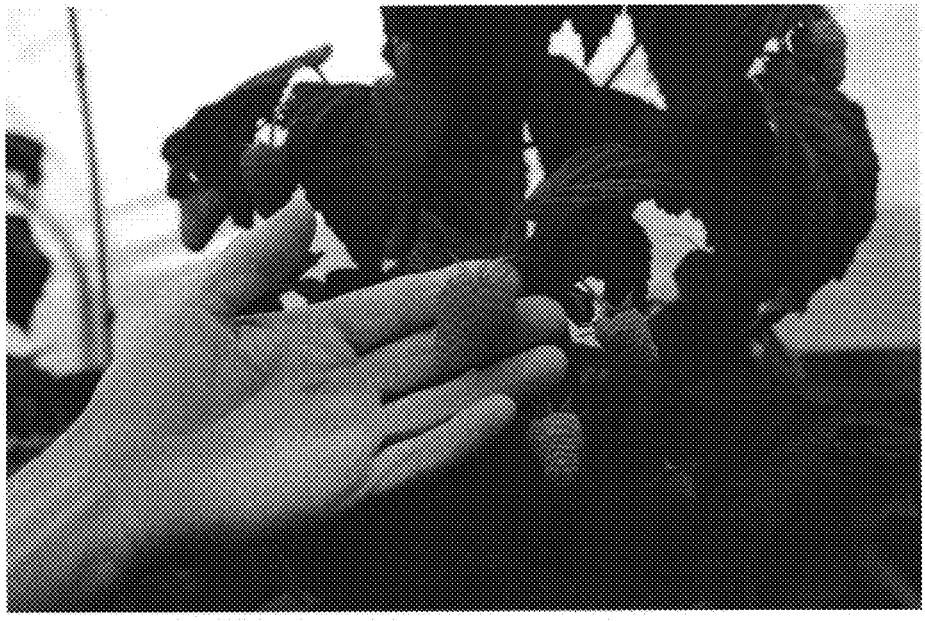
FIG. 3 illustrates the mature and immature fruits of the new variety.
Figure 4:
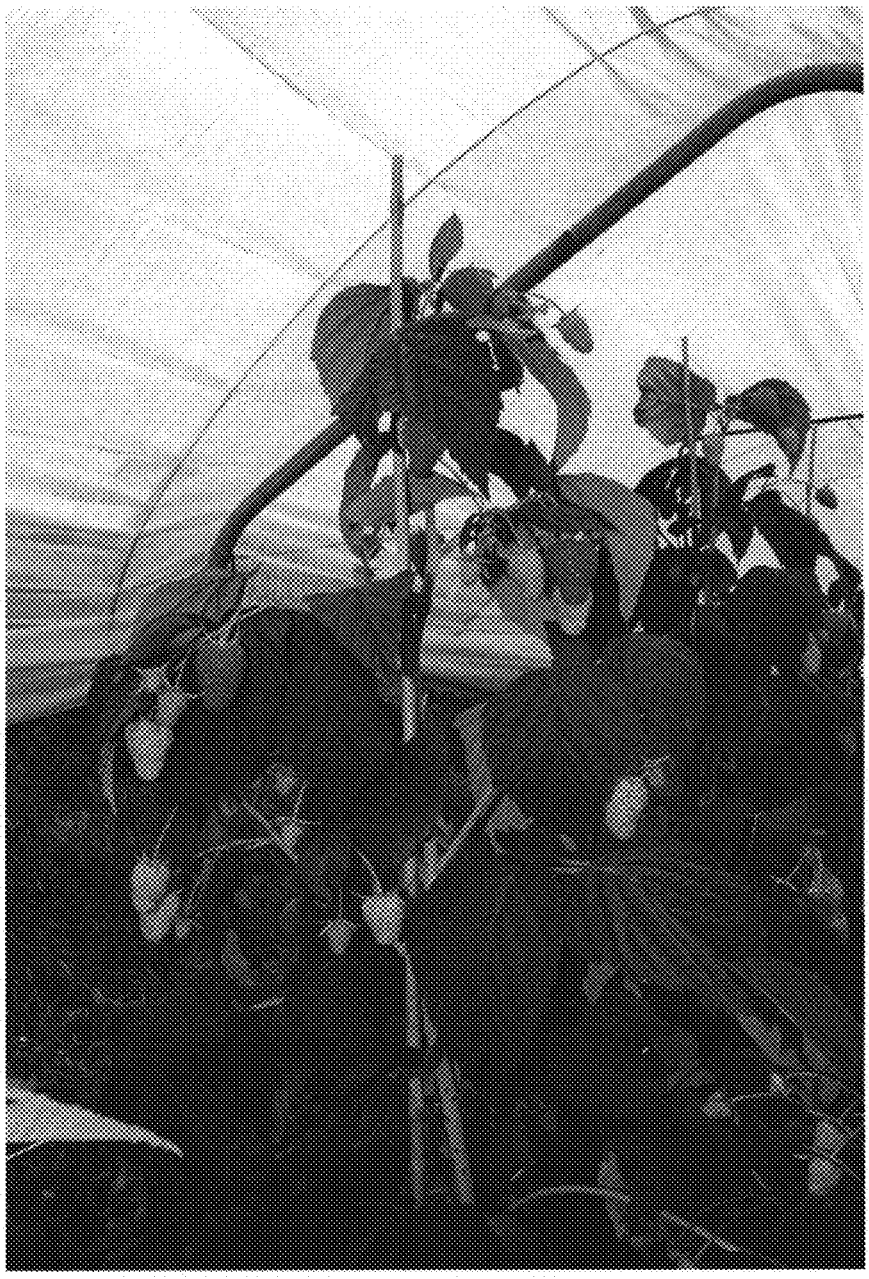
FIG. 4 is a photograph of a fruiting plant of the new variety.
Figure 5:
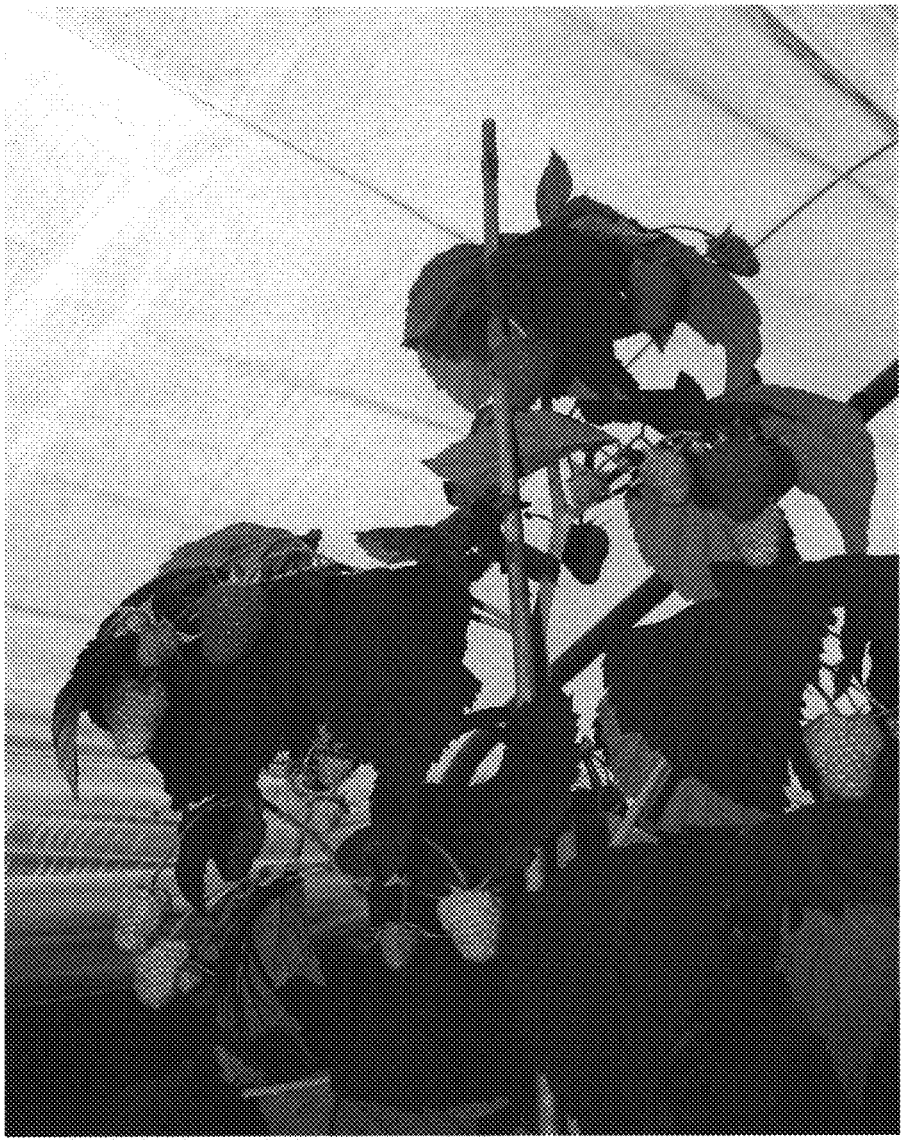
FIG. 5 is a photograph of a fruiting plant of the new variety.
Figure 6:
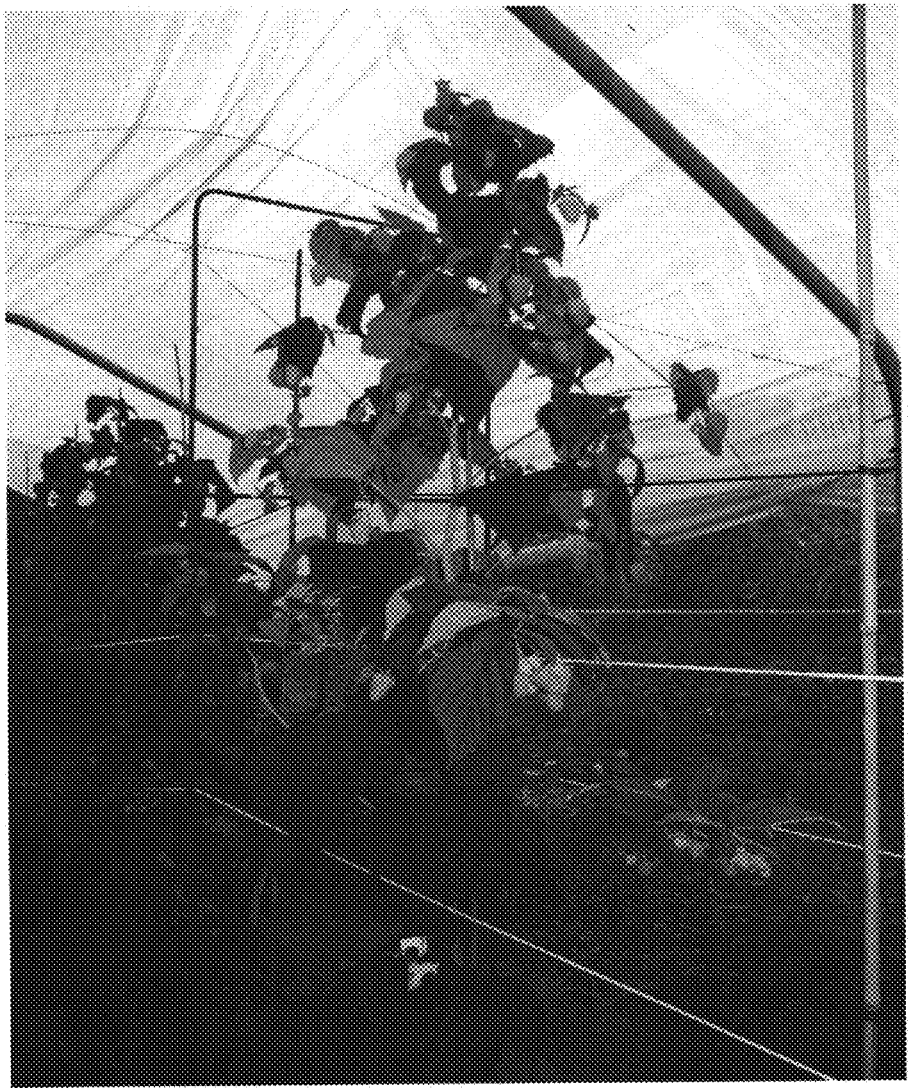
FIG. 6 is a photograph of a fruiting plant of the new variety.
Figure 7:
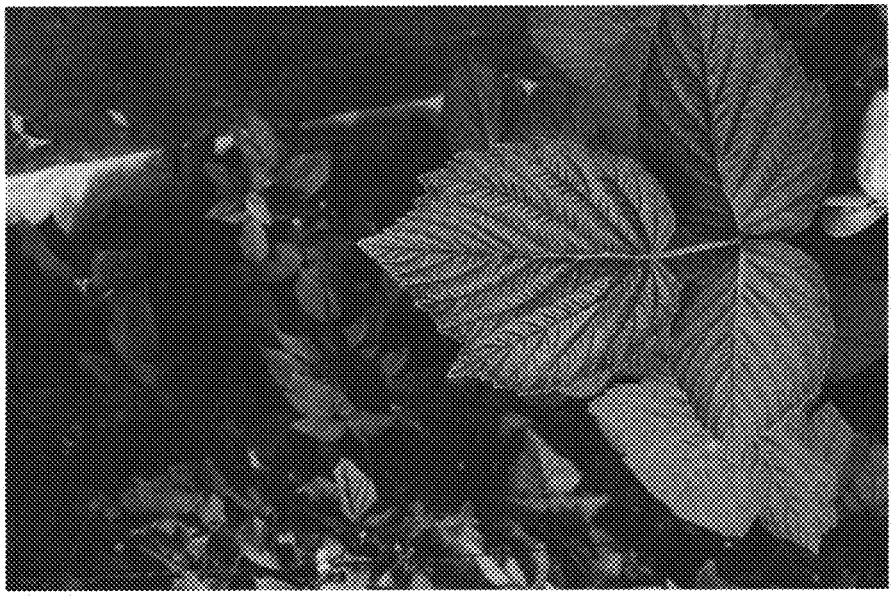
FIG. 7 illustrates the leaves of the new variety.
Figure 8:
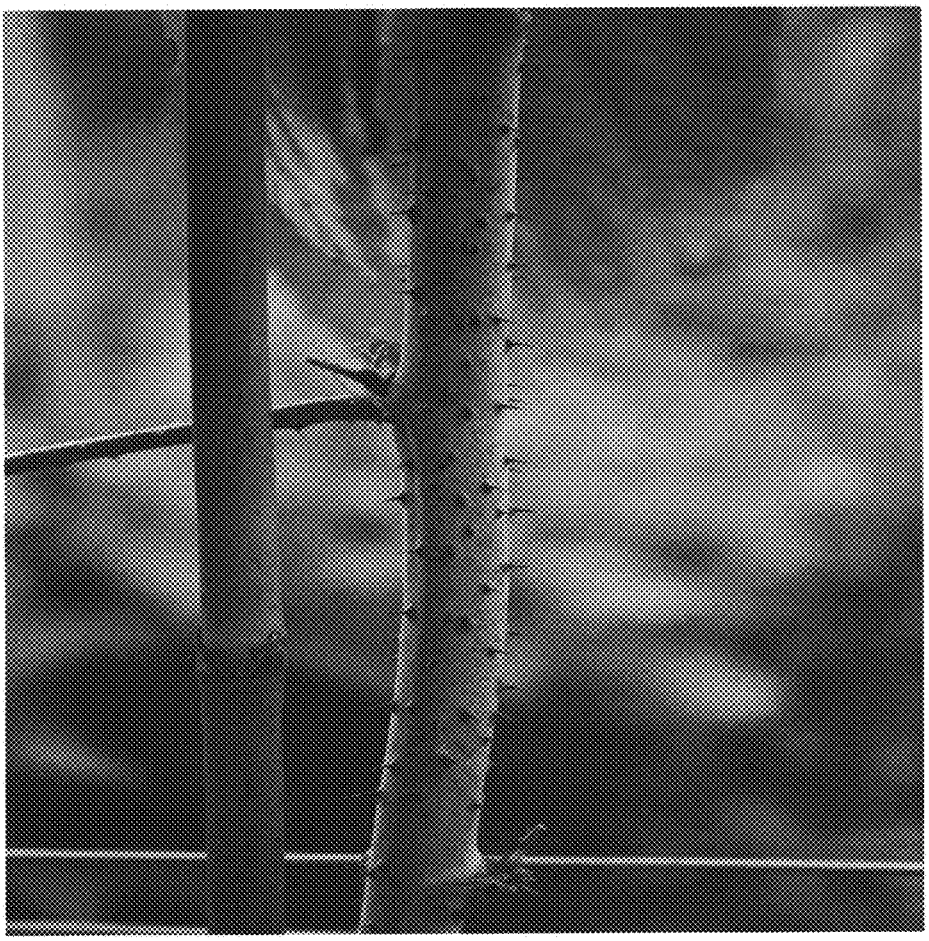
FIG. 8 illustrates the thorns of 'BP 1522'.

'BP 1522' has not been observed under all possible environmental conditions. The phenotype may vary somewhat with variations in environment, such as temperature, day length, and light intensity. However, there is no variance in genotype.

In the following description, color references are made to The Royal Horticultural Society Colour Chart (Fifth Edition, 2007), except where general terms of ordinary dictionary significance are used. Plants of the new variety were grown in 10 liter pots in a greenhouse tunnel covered with plastic in Trento, Italy, and the plants were approximately 1 year old when described. The measurements were taken under natural light in the greenhouse. Further, unless indicated otherwise, primocane descriptions are used throughout.

Plant:

*Primary use*.—'BP 1522' is primarily grown for its primocane fruit for fresh market purposes.

*Time to initiate roots*.—14 days at 18° C., under mist.

*Time to produce a rooted plant*.—45 days, including acclimatization time.

*Rooting habit*.—Fast and without the need to use a rooting promoter.

*Form*.—Spreading and symmetrical.

*Height (from soil to top of plant)*.—160-170 cm.

*Plant diameter*.—60-70 cm.

*Vigor*.—Medium.

*Disease/pest resistance*.—None observed to date.

*Weather tolerance*.—As 'BP 1522' has been protected by a greenhouse environment, no weather tolerance has been observed to date.

*Primocane*.—Average number of canes per plant: One. Average length: 160-170 cm. Average diameter: 0.8-1.0 cm. Fruiting cane color: 142A. Dormant cane color: 166A. Number of fruiting laterals per cane: Numerous. Internode length: 5-7 cm. Young shoot color: 142A.

*Thorn*.—Density: Medium. Length: 2.5 cm. Color: 187B. Texture: Relatively hard. Tip attitude: Downward sloping.

*Foliage*.—Arrangement: Compound. Compound Leaf: Average length: Approximately 25 cm. Average width: Approximately 22 cm. Number of leaves per stem: Usually 3, sometimes 5. Fragrance: None present.

*Petiole*.—Length: 8-10 cm. Diameter: 3 mm. Color: 142A. Texture: Very thin spines present — approximately 10-25 per petiole.

*Young leaflet color*.—Upper surface: 144C. Lower surface: 144D.

*Mature leaflet color*.—Upper surface: 142B. Lower surface: 142D.

*Lateral leaflets*.—Length: 9-10 cm. Width: 6-7 cm. Shape of leaf (generally): Ovate. Shape of apex: Acuminate. Shape of base: Cordate. Texture: Soft. Margin type: Doubly serrate.

*Terminal leaflets*.—Length: 13-14 cm. Width: 9-10 cm. Shape of leaf (generally): Ovate. Shape of apex: Acuminate. Shape of base: Cordate. Texture: Soft. Aspect: More downwardly sloping than lateral leaflets. Margin type: Doubly serrate.

*Veins*.—Appearance: Pronounced; reticulate generally and cross-venulate near the margins. Upper surface color: 144C. Lower surface color: 144D.

*Fruit*.—Harvest season: When planted in May, August 15$^{th}$ through October 15$^{th}$ on primocanes in Trento, Italy. Fruit bearing type: Mainly current year's cane in Autumn. Number of fruit per fruiting lateral: 18-30. Average number of fruit per node: 4-5. Average overall fruit yield per plant: 1.5-2 kg when grown in a pot. Immature color: 43D. Maturing color: 44A. Mature color: 45A. Taste: Very nice; similar to 'Tulameen' (unpatented). Length: 3-4 cm. Width: 2.5-3.0 cm. Overall shape: Conical; heart-shaped. Glossiness: Good; similar to 'Tulameen'. Weight: 6-7 g per fruit on first harvest, then decreases to 5 g. Drupelet: Average number per fruit: 100-200. Arrangement: Regular. Weight: 45 mg each. Width: 3-4 mm. Flesh firmness: Good. Skin firmness: Very good. Receptacle/torus length: 1.8-2.0 cm. Receptacle/torus width: 0.8-0.9 cm. Adherence of berry to receptacle: Very easy to detach, even when not fully ripe. Pubescence: Average. Percent soluble solids: 9° Bx. Titratable acidity: 39 mEq/100 g. Penetrometer reading: 0.8-1.0 kg/cm$^2$. Shelf-life: Fruit maintains dryness, shape, and firmness very well once picked.

*Reproductive organs*.—Pistil number per flower: 90-120. Pistil size: Average. Stamen number per flower: 90-130. Stamen size: Average.

*Flowers*.—Timing: In Trento, Italy, the primocanes of 'BP 1522' begin flowering at the beginning of August — one week to 10 days before 'Sugana'. Number of flowers per plant: 180-230. Color: 155D. Flower height: 0.7 cm. Flower diameter: 2.5 cm. Pedicels: Not applicable. Peduncle: Length: 4-6 cm. Surface texture: Slightly thorny. Color: 145A. Fragrance: None present. Longevity: Medium. Seeds: Shape: Bean-shaped. Length: 3 mm. Diameter: 1.5 mm. Color: 164A.

I claim:

1. A new and distinct variety of *Rubus* plant named 'BP 1522' as herein described and illustrated.

* * * * *